United States Patent [19]

Makino et al.

[11] Patent Number: 5,763,365
[45] Date of Patent: Jun. 9, 1998

[54] FLUOROPROPYLTHIAZOLINE DERIVATIVES AND HERBICIDES

[75] Inventors: Kenji Makino; Hideaki Suzuki; Takeshi Nagaoka; Toshio Niki; Yoshiyuki Kusuoka; Toshimasa Hamada, all of Funabashi; Tsutomu Nawamaki, Shiraoka-machi; Shigeomi Watanabe, Shiraoka-machi; Yoichi Ito, Shiraoka-machi; Kazuhisa Sudo, Saitama, all of Japan

[73] Assignee: Nissan Chemical Industries, Ltd., Tokyo, Japan

[21] Appl. No.: 669,380

[22] PCT Filed: Jan. 10, 1995

[86] PCT No.: PCT/JP95/00011

§ 371 Date: Jul. 11, 1996

§ 102(e) Date: Jul. 11, 1996

[87] PCT Pub. No.: WO95/18806

PCT Pub. Date: Jul. 13, 1995

[30] Foreign Application Priority Data

Jan. 11, 1994 [JP] Japan .................. 6-001047
Dec. 14, 1994 [JP] Japan .................. 6-310585

[51] Int. Cl.$^6$ .................. C07D 403/12; A01N 43/66
[52] U.S. Cl. .................. 504/213; 544/212
[58] Field of Search .................. 544/212; 504/213

[56] References Cited

U.S. PATENT DOCUMENTS 5,152,824  10/1992  Makino et al. .................. 71/91
5,500,406  3/1996  Makino et al. .................. 504/215

FOREIGN PATENT DOCUMENTS

WO93/00336  1/1993  WIPO.

*Primary Examiner*—John M. Ford
*Attorney, Agent, or Firm*—Oblon, Spivak, McClelland, Maier & Neustadt, P.C.

[57] ABSTRACT

A fluoropropylthiazoline represented by the formula (1), a herbicide containing it and intermediates for it.

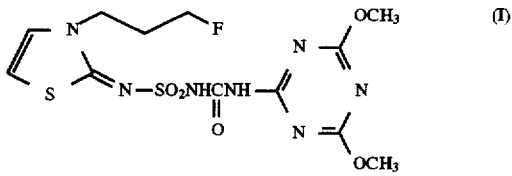

4 Claims, No Drawings

FLUOROPROPYLTHIAZOLINE DERIVATIVES AND HERBICIDES

This is a 371 of PCT/JPA5/00011, filed Jan. 10, 1995.

TECHNICAL FIELD

The present invention relates to novel fluoropropylthiazoline derivatives and herbicides containing such derivatives as active ingredients.

BACKGROUND TECHNIQUE

A herbicide is indispensable for protection of important crop plants such as rice, wheat, corn, soybean, cotton and sugar beet from damage by weeds and increase in their harvests. Especially, in recent years, selective herbicides which can be applied simultaneously to foliages of weeds and a useful crop plant coexisting in the same agricultural field and kill only the weeds selectively with no harm to the crop plant, are desired. In view of prevention of environmental pollution and reduction in economic costs for transportation and application, compounds having high herbicidal effects at as low doses as possible have been sought and researched over years. Some compounds having such characteristics are now used as selective herbicides. However, more excellent and new compounds having such properties are still in demand.

As a prior art analogous to the compound of the present invention, International Patent Publication WO93/00336 discloses substituted thiazolines. However, it does not disclose at all that the compound of claim 1 is safe for beet as well as exhibits an excellent herbicidal effect. In short, the compound of the present invention has a specific effect totally inconceivable from the above-mentioned prior art.

DISCLOSURE OF THE INVENTION

During years of studies for development of herbicides selective for important crops, the present inventors examined a number of compounds on their herbicidal properties, seeking a compound having higher herbicidal effect and selectivity. As a result, they found that a fluoropropylthiazoline derivative represented by the formula (I):

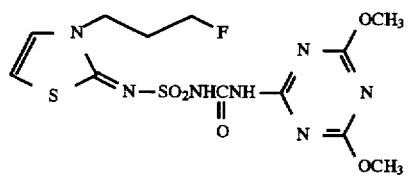

and its agriculturally suitable salts (hereinafter referred to as compounds of the present invention) have remarkably strong herbicidal effects on various weeds and are quite safe for sugar beet, which is an important crop plant, in soil treatment, soil incorporation treatment and foliage treatment. The present invention has been accomplished on the basis of this discovery.

The compounds of the present invention can be prepared readily in accordance with any of the following Reaction Schemes 1 to 6.

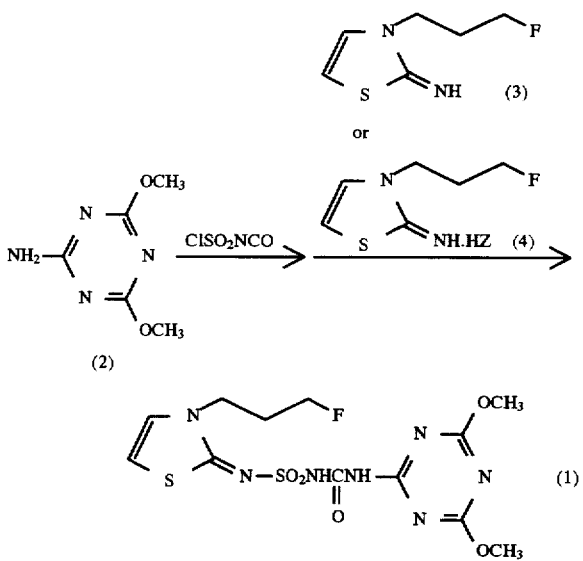

[wherein Z is a halogen atom.]

Namely, the triazine derivative (2) is allowed to react with chlorosulfonyl isocyanate in a solvent such as tetrahydrofuran, dimethoxyethane, acetonitrile, propionitrile, dimethylformamide, dichloromethane, ethylene dichloride, benzene or toluene, and then with the 2-imino-3-fluoropropylthiazoline (3) or (4) in the presence of a base such as triethylamine, pyridine, sodium hydride, sodium methoxide, sodium ethoxide, sodium hydroxide, potassium hydroxide or potassium carbonate, to prepare the compound (1) of the present invention.

Chlorosulfonyl isocyanate is used in an amount of from 0.7 to 1.3 mols per mol of the triazine derivative (2). The reaction temperature may be arbitrarily selected within a range of from −50° C. to 80° C.

The 2-imino-3-fluoropropylthiazoline (3) or (4) is used in an amount of from 0.7 to 1.3 mols per mol of the triazine derivative (2), and the base is used in an amount of from 0.5 to 4.0 mols per mol of the 2-imino-3-fluoropropylthiazoline (3) or (4). The reaction temperature may be arbitrarily selected within a range of from −50° C. to 100° C.

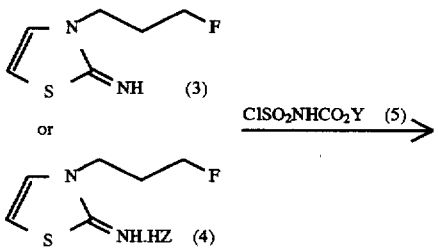

[Reaction Scheme 2] -continued

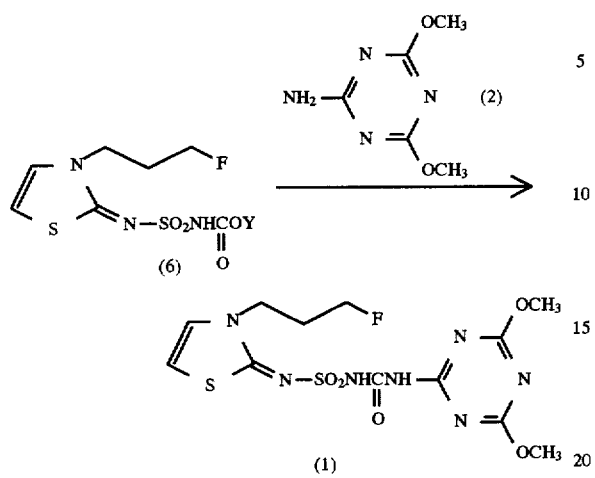

[wherein Z is the same as defined above, and Y is a lower alkyl with a carbon number of from 1 to 6 or a phenyl group.]

Namely, the 2-imino-3-fluoropropylthiazoline (3) or (4) is allowed to react with phenyl N-chlorosulfonylcarbamate (5: Y=a phenyl group) or an alkyl N-chlorosulfonylcarbamate (5: Y=a lower alkyl group), by using from 0.5 to 3.0 mols, preferably from 0.9 to 1.2 mols of the carbamate derivative (5), per mol of the 2-imino-3-fluoropropylthiazoline (3) or (4).

The reaction temperature may be arbitrarily selected within a range of from –50° C. to 100° C., and is preferably within a range of from –40° C. to 30° C.

This reaction is carried out by using various bases. Such a base is used in an amount of from 0.5 to 4.0 mols per mol of the 2-imino-3-fluoropropylthiazoline (3) or (4).

Suitable bases are organic bases such as triethylamine and pyridine, metal hydrides such as sodium hydride, inorganic bases such as sodium hydroxide, potassium hydroxide and potassium carbonate, and metal alkoxides such as sodium methoxide and sodium ethoxide.

Solvents suitable for this reaction are solvents inert in this reaction, for example, aromatic hydrocarbons such as benzene, toluene and xylene, halogenated hydrocarbons such as dichloromethane, chloroform and ethylene dichloride, ethers such as ethyl ether, isopropyl ether, dioxane and tetrahydrofuran, nitriles such as acetonitrile and propionitrile, hydrocarbons such as petroleum ether, petroleum benzin and heptane, ketones such as acetone and methyl ethyl ketone, esters such as ethyl acetate, and amides such as dimethylformamide, dimethylacetamide and hexamethylphosphoric triamide. These solvents may be used singly or in combination. Particularly preferred are ethers and amides.

Then, phenyl 3-fluoropropylthiazoline-2-iminosulfonylcarbamate (6: Y=a phenyl group) or an alkyl 3-fluoropropylthiazoline-2-iminosulfonylcarbamate (6: Y=a lower alkyl group) and the triazine derivative (2) are heated in various solvents such as benzene, toluene, xylene and dioxane to prepare the compound (1) of the present invention.

[Reaction Scheme 3]

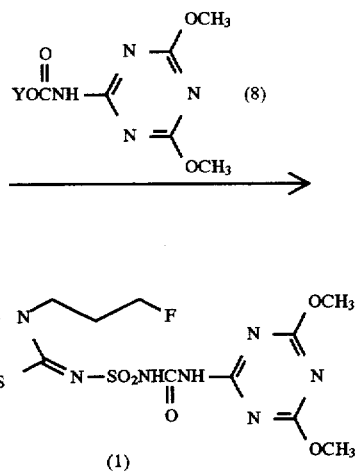

[wherein Y is the same as defined above.]

Namely, 3-fluoropropylthiazoline-2-iminosulfonamide (7) is allowed to react with the carbamate derivative (8) in a solvent such as acetone, acetonitrile or dioxane in the presence of an inorganic base such as potassium carbonate or an organic base such as triethylamine or 1,8-diazabicyclo [5.4.0]-7-undecene (DBU), to prepare the compound (1) of the present invention.

[Reaction Scheme 4]

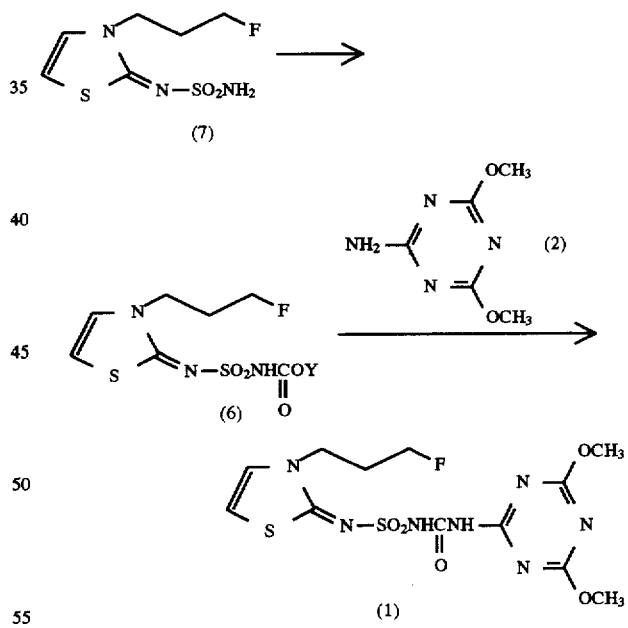

[wherein Y is the same as defined above.]

Namely, 3-fluoropropylthiazoline-2-iminosulfonamide (7) is allowed to react with chloroformic ester or carbonic acid ester in a solvent such as acetone, methyl ethyl ketone, acetonitrile, tetrahydrofuran, dimethylformamide or dioxane in the presence of a base such as potassium carbonate or triethylamine, to prepare phenyl 3-fluoropropylthiazoline-2-iminosulfonylcarbamate (6: Y=a phenyl group) or an alkyl 3-fluoropropylthiazoline-2-iminosulfonylcarbamate (6: Y=a lower alkyl group). Then, it is heated together with the triazine derivative (2) in a solvent such as benzene, toluene, xylene or dioxane to prepare the compound (1) of the present invention.

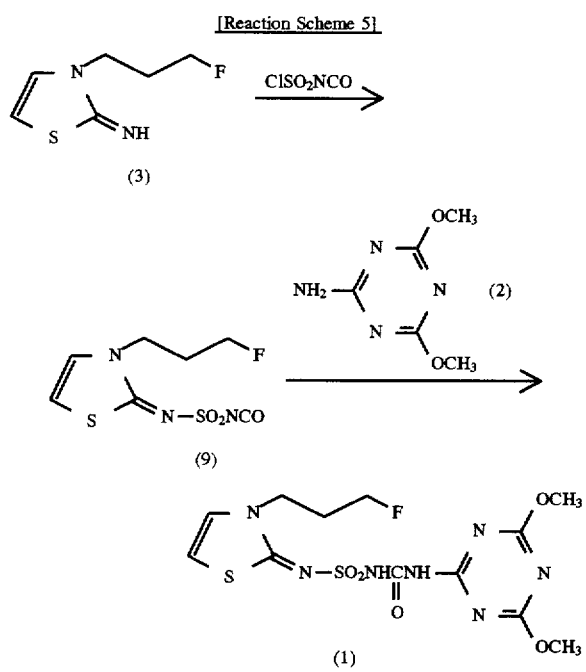

Namely, 2-imino-3-fluoropropylthiazoline (3) is allowed to react with chlorosulfonyl isocyanate, by using from 0.7 to 2.0 mols, preferably from 0.9 to 1.5 mols of chlorosulfonyl isocyanate, per mol of 2-imino-3-fluoropropylthiazoline (3).

In this reaction, an intermediate 1-[3-(3-fluoropropyl) thiazoline-2-iminosulfonyl]-3-chlorosulfonylurea, is synthesized at a reaction temperature within a range of from −50° C. to 50° C. Subsequent heating at a reaction temperature suitable for rearrangement reaction and removal of the consequential hydrogen chloride within a range of from 60° C. to 150° C. converts the intermediate into 3-fluoropropylthiazoline-2-iminosulfonyl isocyanate (9).

Solvents suitable for this reaction are those inert in this reaction, for example, aromatic hydrocarbons such as benzene, toluene and xylene, aromatic halides such as chlorobenzene and dichlorobenzene, aromatic nitro compounds such as nitrobenzene, halogenated hydrocarbons such as ethylene dichloride, ethers such as dioxane and tetrahydrofuran, nitrites such as acetonitrile and propionitrile, hydrocarbons such as petroleum ether, petroleum benzin and heptane, ketones such as methyl ethyl ketone, and esters such as ethyl acetate. These solvents may be used singly or in combination. Particularly preferred are aromatic halides and aromatic hydrocarbons.

Then, 3-fluoropropylthiazoline-2-iminosulfonyl isocyanate (9) is allowed to react with the triazine derivative (2) in a solvent such as dichloromethane, chloroform, ethylene dichloride, ethyl ether, dioxane, acetonitrile, acetone, methyl ethyl ketone, benzene, toluene, xylene, chlorobenzene or dichlorobenzene to prepare the compound (1) of the present invention.

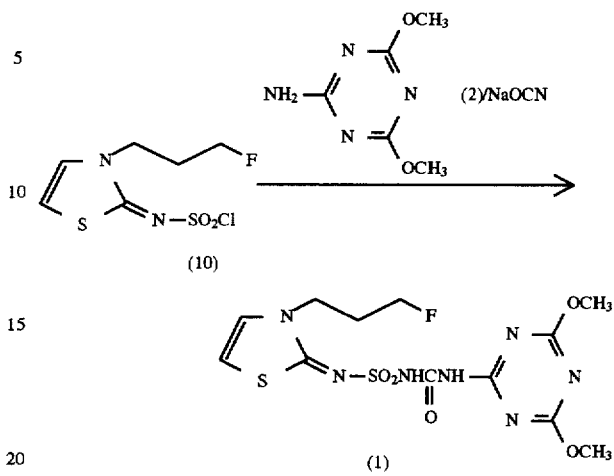

Namely, 3-fluoropropylthizoline-2-iminosulfonyl chloride (10) is allowed to react with the triazine derivative (2) and sodium cyanate, by using from 0.5 to 1.5 mols of the triazine (2) and from 1 to 3 mols of sodium cyanate, per mol of 3-fluoropropylthiazoline-2-iminosulfonyl chloride (10). The reaction temperature may be arbitrarily selected within a range of from −20° C. to 50° C., and is preferably within a range of from 5° C. to 30° C.

In this reaction, various bases may be used. Such a base is used in an amount of from 1 to 3 mols per mol of 3-fluoropropylthiazoline-2-iminosulfonyl chloride (10).

Suitable bases are organic bases such as triethylamine and pyridine, metal alkoxides such as sodium methoxide and sodium ethoxide, metal hydrides such as sodium hydride, and inorganic bases such as sodium hydroxide, potassium hydroxide and potassium carbonate, particularly preferred are organic bases.

Solvents suitable for this reaction are those inert in this reaction, for example, aromatic hydrocarbons such as benzene, toluene and xylene, halogenated hydrocarbons such as dichloromethane, chloroform and ethylene dichloride, ethers such as dioxane and tetrahydrofuran, nitrites such as acetonitrile and propionitrile, ketones such as acetone and methyl ethyl ketone, and amides such as dimethylformamide, dimethylacetamide and hexamethylphosphoric triamide. These solvents may be used singly or in combination. Particularly preferred are nitriles and amides.

3-Fluoropropylthiazoline-2-iminosulfonyl chloride (10) can be synthesized, for example, by the method represented by the following Reaction Scheme 7 from a 2-imino-3-fluoropropylthiazoline (3) or (4).

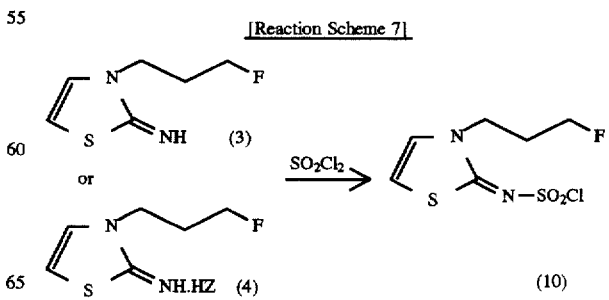

[wherein Z is the same as defined above.]

In Reaction Scheme 7, the amount of sulfuryl chloride may be selected arbitrarily within a range between an equimolar amount and an excessive amount.

In this reaction, various bases may be used. Such a base is used in an amount of from 0.8 to 5 mols per mol of the 2-imino-3-fluoropropylthiazoline (3) or (4).

Suitable bases are organic bases such as triethylamine and pyridine, metal alkoxides such as sodium methoxide and sodium ethoxide, metal hydrides such as sodium hydride, and inorganic bases such as sodium hydroxide, potassium hydroxide and potassium carbonate. Particularly preferred are organic bases.

Solvents suitable for this reaction are those inert in this reaction, for example, aromatic hydrocarbons such as benzene, toluene and xylene, halogenated hydrocarbons such as dichloromethane, chloroform and ethylene dichloride, ethers such as dioxane and tetrahydrofuran, nitrites such as acetonitrile and propionitrile, ketones such as acetone and methyl ethyl ketone, and amides such as dimethylformamide, dimethylacetamide and hexamethylphosphoric triamide.

These solvents may be used singly or in combination.

The reaction temperature may be arbitrarily selected within a range of from −50° C. to 100° C., and is preferably within a range of from −20° C. to 50° C.

3-Fluoropropylthiazoline-2-iminosulfonamide (7) can be synthesized by the methods represented by the following Reaction Schemes 8 and 9.

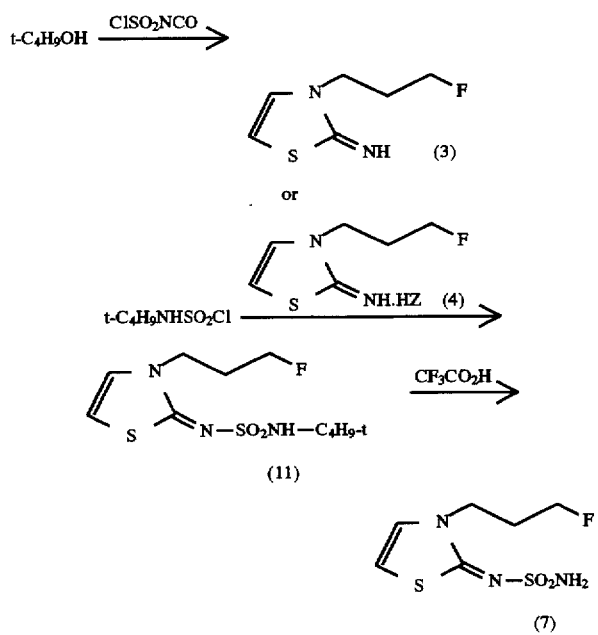

[wherein Z is the same as defined above.]

In Reaction Scheme 8, the reaction of tert-butanol with chlorosulfonyl isocyanate can be carried out by well-known methods, for example, by reference to Japanese Unexamined Patent Publication No. 101323/1975.

The 2-imino-3-fluoropropylthiazoline (3) or (4) is allowed to react with tert-butylsulfamoyl chloride, by using from 0.5 to 3.0 mols, preferably from 0.9 to 1.2 mols of tert-butylsulfamoyl chloride, per mol of the 2-imino-3-fluoropropylthiazoline (3) or (4).

The reaction temperature may be arbitrarily selected within a range of −50° C. to 100° C., and is preferably within a range of from −40° C. to 30° C.

In this reaction, various bases are used. Such a base is used in an amount of from 0.5 to 4.0 mols, preferably from 0.8 to 2.5 mols, per mol of the 2-imino-3-fluoropropylthiazoline (3) or (4). Suitable bases are, for example, metal hydrides such as sodium hydride, organic bases such as triethylamine and pyridine, inorganic bases such as sodium hydroxide, potassium hydroxide and potassium carbonate, and metal alkoxides such as sodium methoxide and sodium ethoxide. Particularly preferred are organic bases.

Solvents suitable for this reaction are those inert in this reaction, for example, aromatic hydrocarbons such as benzene, toluene and xylene, halogenated hydrocarbons such as dichloromethane, chloroform and ethylene dichloride, ethers such as ethyl ether, isopropyl ether, dioxane and tetrahydrofuran, nitriles such as acetonitrile and propionitrile, hydrocarbons such as petroleum ether, petroleum benzin and heptane, ketones such as acetone and methyl ethyl ketone, esters such as ethyl acetate, and amides such as dimethylformamide, dimethylacetamide and hexamethylphosphoric triamide. These solvents may be used singly or in combination. Particularly preferred are ethers and amides.

In Reaction Scheme 8, the tert-butyl group is removed by using trifluoroacetic acid. The amount of trifluoroacetic acid may be arbitrarily selected within a range between an equimolar amount and an excessive amount. Trifluoroacetic acid may be used as a solvent without any problem.

The reaction temperature may be selected arbitrarily within a range of from −50° C. to 80° C., and is preferably within a range of from −20° C. to 30° C.

When a solvent is used in this reaction, solvents inert in this reaction, for example, aromatic hydrocarbons such as benzene, toluene and xylene, halogenated hydrocarbons such as dichloromethane, chloroform and ethylene dichloride, ethers such as ethyl ether, isopropyl ether, dioxane and tetrahydrofuran, nitriles such as acetonitrile and propionitrile, hydrocarbons such as petroleum ether, petroleum benzin and heptane, ketones such as acetone and methyl ethyl ketone, esters such as ethyl acetate, and amides such as dimethylformamide, dimethylacetamide and hexamethylphosphoric triamide, may be mentioned. These solvents may be used singly or in combination.

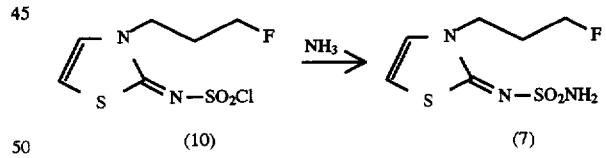

In Reaction Scheme 9, the amount of ammonia may be selected arbitrarily within a range between 2 mols per mol of 3-fluoropropylthiazoline-2-iminosulfonyl chloride (10) and an excessive amount. Liquid, gaseous or aqueous ammonia may be used without any problem. The reaction temperature may be selected arbitrarily within a range of from −76° C. to 80° C.

Solvents suitable for this reaction are those inert in this reaction, for example, aromatic hydrocarbons such as benzene, toluene and xylene, halogenated hydrocarbons such as dichloromethane, chloroform and ethylene dichloride, ethers such as ethyl ether, isopropyl ether, dioxane and tetrahydrofuran, nitriles such as acetonitrile and propionitrile, hydrocarbons such as petroleum ether, petroleum benzin and heptane, ketones such as acetone and methyl ethyl ketone, esters such as ethyl acetate, amides such as dimethylformamide, dimethylacetamide and hexamethylphosphoric triamide, and alcohols such as methanol and ethanol. These solvents may be used singly or in combination.

The most suitable solvent varies depending on the state of ammonia.

The intermediates used for the present invention, phenyl 3-fluoropropylthiazoline-2-iminosulfonylcarbamate (6: Y=a phenyl group), an alkyl 3-fluoropropylthiazoline-2-iminosulfonylcarbamate (6: Y=a lower alkyl group), 3-fluoropropylthiazoline-2-iminosulfonamide (7), 3-fluoropropylthiazoline-2-iminosulfonyl isocyanate (9) and 3-fluoropropylthiazoline-2-iminosulfonyl chloride (10), are also novel compounds.

Phenyl N-chlorosulfonylcarbamate (5: Y=a phenyl group) and an alkyl N-chlorosulfonylcarbamate (5: Y=a lower alkyl group) in Reaction Scheme 2 can be synthesized by well-known methods, for example, by reference to Chemische Berichte, vol. 96, p. 56 (1963).

The 2-imino-3-fluoropropylthiazoline (3) or (4) used as the starting material in this reaction can be synthesized, for example, by reference to U.S. Pat. No. 4,237,302. Reaction Scheme 10 represents synthesis of 2-imino-3-fluoropropylthiazoline (3).

[Reaction Scheme 10]

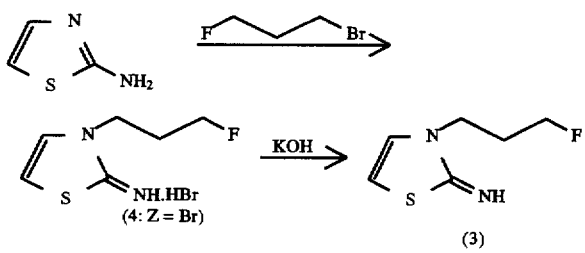

BEST MODE FOR CARRYING OUT THE INVENTION

Now, synthesis of the compounds of the present invention will be described in detail with reference to Reference Example and Examples. However, it should be understood that the present invention is by no means restricted by such specific Examples.

[REFERENCE EXAMPLE 1]

Synthesis of 2-imino-3-(3-fluoropropyl)thiazolines (3) and (4: Z=Br)

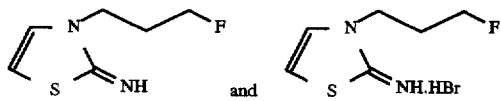

5 g (50 mmol) of 2-aminothiazole was dissolved in 15 ml of dimethylformamide, and 8.8 g (62.4 mmol) of 1-bromo-3-fluoropropane was added at room temperature. The reaction mixture was heated with stirring at 80° C. for 7.5 hours and then allowed to cool to room temperature. After addition of 300 ml of ethyl acetate, the reaction mixture was stirred at room temperature for 10 minutes. The resulting oily substance was separated from the ethyl acetate solution by decantation, and the same operation was repeated twice. The oily substance was crystallized by adding ethyl acetate and a small amount of methanol and filtered off to obtain 5.5 g of 2-imino-3-(3-fluoropropyl)thiazoline hydrobromide (4: Z=Br). Melting point 153°–155° C.

Then, 1.21 g (5 mmol) of 2-imino-3-(3-fluoropropyl) thiazoline hydrobromide (4: Z=Br) was stirred with 0.33 g (5 mmol) of 85% potassium hydroxide in 20 ml of methanol at room temperature for 1 hour. After the methanol was distilled off under reduced pressure, 20 ml of chloroform was added to the residue, and precipitated insolubles were filtered out. The chloroform in the filtrate was distilled off under reduced pressure to obtain 0.8 g of 2-imino-3-(3-fluoropropyl)thiazoline (3) as an oily substance. The chemical shifts by NMR were as follows. (60 MHz) δ(ppm, $CDCl_3$): 1.6–2.7(2H,m), 3.84(2H,t,J=6.8 Hz), 4.50(2H,dt,J= 47.0 Hz,5.6 Hz), 5.74(1H,d,J=4.7 Hz), 6.40(1H,d,J=4.7 Hz), 5.5–6.8(1H,br)

15 g (62.2 mmol) of 2-imino-3-(3-fluoropropyl)thiazoline hydrobromide (4: Z=Br) was dissolved in 150 ml of water, and 8.59 g (62.2 mmol) of anhydrous potassium carbonate was added. The mixture was stirred at room temperature for 10 minutes. The mixture was extracted with 150 ml of chloroform 4 times, and the organic layer was washed with saturated aqueous salt solution and dried over anhydrous sodium sulfate. The solvent was distilled off under reduced pressure to obtain 9.45 g of 2-imino-3-(3-fluoropropyl) thiazoline (3) as an oily substance.

EXAMPLES

[EXAMPLE 1]

Synthesis of 1-[3-(3-fluoropropyl)thiazoline-2-iminosulfonyl]-3-(4,6-dimethoxytriazin-2-yl)urea (1)

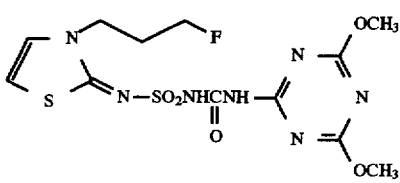

A method)

0.58 g (3.72 mmol) of 2-amino-4,6-dimethoxytriazine (2) was dissolved in 100 ml of dry tetrahydrofuran, and 0.53 g (3.75 mmol) of chlorosulfonyl isocyanate was added dropwise at room temperature. After 10 minutes of stirring, a mixture of 1.0 g (4.15 mmol) of 2-imino-3-(3-fluoropropyl) thiazoline hydrobromide (4: Z=Br), 0.84 g (8.32 mmol) of triethylamine and 10 ml of tetrahydrofuran was added, and the resulting mixture was stirred at room temperature for 1 hour. The solvent was distilled off under reduced pressure, and after addition of 100 ml of water, the residue was extracted with 150 ml of chloroform three times. The chloroform layer was washed with 50 ml of water and then dried over anhydrous sodium sulfate. After the solvent was distilled off under reduced pressure, the residue was crystallized by adding ethyl ether and acetonitrile, and filtered off to obtain 0.4 g of the desired product, 1-[3-(3-fluoropropyl)thiazoline-2-iminosulfonyl]-3-(4,6-dimethoxytriazin-2-yl)urea (1). Melting point 175°–177° C.

B method)

0.78 g (5 mmol) of 2-amino-4,6-dimthoxytriazine (2) was dissolved in 30 ml of dry tetrahydrofuran, and 0.71 g (5 mmol) of chlorosulfonyl isocyanate was added dropwise at room temperature. After 30 minutes of stirring, a mixture of 0.8 g (5 mmol) of 2-imino-3-(3-fluoropropyl)thiazoline (3), 0.55 g (5.4 mmol) of triethylamine and 20 ml of tetrahydrofuran was added, and the resulting mixture was stirred at room temperature for 30 minutes. Then, the solvent was distilled off under reduced pressure. After addition of 100 ml of water, the residue was extracted with 100 ml of chloroform three times. Then, the solvent was distilled off under reduced pressure, and the resulting residue was purified by preparative thin layer chromatography (developing solvent: ethyl acetate). The resulting roughly purified product was crystallized by adding ether and acetonitrile, and filtered off to obtain 0.21 g of the desired product, 1-[3-(3-fluoropropyl) thiazoline-2-iminosulfonyl]-3-(4,6-dimethoxytriazin-2-yl) urea (1).

C method)

0.17 g (1.1 mmol) of 2-amino-4,6-dimethoxytriazine (2) was dissolved in 30 ml of dry tetrahydrofuran, and 0.15 g (1.1 mmol) of chlorosulfonyl isocyanate was added dropwise at room temperature. After 30 minutes of stirring, this solution was added to a mixture of 0.26 g (1.1 mmol) of 2-imino-3-(3-fluoropropyl)thiazoline hydrobromide (4: Z=Br), 0.24 g (2.4 mmol) of triethylamine and 30 ml of tetrahydrofuran, and the resulting mixture was stirred at room temperature for 30 minutes. Then, the solvent was distilled off under reduced pressure, and after addition of 50 ml of water, the residue was extracted with 60 ml of chloroform three times. The chloroform layer was washed with 50 ml of water and dried over anhydrous sodium sulfate. After the solvent was distilled off under reduced pressure, the residue was crystallized by adding ethyl ether and acetonitrile, and filtered off to obtain 0.22 g of the desired product, 1-[3-(3-fluoropropylthiazoline-2-iminosulfonyl]-3-(4,6-dimethoxytriazin-2-yl)urea (1).

D method)

0.61 g (3.9 mmol) of 2-amino-4,6-dimethoxytriazine (2) was dissolved in 30 ml of dry tetrahydrofuran, and 0.56 g (3.9 mmol) of chlorosulfonyl isocyanate was added dropwise at room temperature. After 30 minutes of stirring, this solution was added to a mixture of 0.63 g (3.9 mmol) of 2-imino-3-(3-fluoropropyl)thiazoline (3), 0.44 g (4.3 mmol) of triethylamine and 50 ml of tetrahydrofuran. The resulting mixture was stirred at room temperature for 30 minutes, and the solvent was distilled off under reduced pressure. After addition of 100 ml of water, the resulting residue was extracted with 100 ml of chloroform three times. The chloroform layer was washed with 50 ml of water and dried over anhydrous sodium sulfate. Then, the solvent was distilled off under reduced pressure. The residue was crystallized by adding ethyl ether and acetonitrile, and filtered off to obtain 1.1 g of the desired product, 1-[3-(3-fluoropropyl) thiazoline-2-iminosulfonyl]-3-(4,6-dimethoxytriazin-2-yl) urea (1).

[EXAMPLE 2]

0.62 g (8.4 mmol) of tert-butanol was dissolved in 6 ml of normal hexane, and 1.18 g (8.4 mmol) of chlorosulfonyl isocyanate was added under cooling with ice. The reaction solution was heated at 50° C. for 5 minutes, and the solvent was distilled off under reduced pressure. To the residue, 30 ml of dry tetrahydrofuran was added. Then, the resulting solution was cooled to −30° C., and a mixture of 2 g (8.3 mmol) of 2-imino-3-(3-fluoropropyl)thiazoline hydrobromide (4: Z=Br), 1.68 g (16.6 mmol) of triethylamine and 20 ml of tetrahydrofuran was added. After 90 minutes of stirring at room temperature, the solvent was distilled off under reduced pressure. After addition of 100 ml of water, the resulting residue was extracted with 100 ml of chloroform three times. The chloroform layer was washed with 50 ml of water and dried over anhydrous sodium sulfate. The solvent was distilled off under reduced pressure, and the resulting crystals were washed with ethyl ether to obtain 0.73 g of N-tert-butyl-[3-(3-fluoropropyl) thiazoline-2-imino]sulfonamide (11). Melting point 103°–105° C.

0.4 g (1.4 mmol) of N-tert-butyl-[3-(3-fluoropropyl) thiazoline-2-imino]sulfonamide (11) was dissolved in 15 ml of trifluoroacetic acid, and the mixture was stirred at room temperature overnight. The trifluoroacetic acid was distilled off under reduced pressure, and the residue was subjected to silica gel chromatography to obtain 0.2 g of [3-(3-fluoropropyl)thiazoline-2-imino]sulfonamide (7). Melting point 70°–73° C.

0.18 g (0.75 mmol) of [3-(3-fluoropropyl)thiazoline-2-imino]sulfonamide (7) and 0.21 g (0.75 mmol) of phenyl N-(4,6-dimethoxytriazin-2-yl)carbamate (8) were dissolved in 20 ml of dry acetonitrile, and 0.12 g (0.79 mmol) of 1,8-diazabicyclo-[5.4.0]-7-undecene (DBU) was added. The resulting mixture was stirred at room temperature for 3 hours and concentrated by distilling off the solvent by half under reduced pressure. Then, 50 ml of water was added thereto. After addition of concentrated hydrochloric acid, the precipitated crystals were filtered off and washed with ether to obtain 0.17 g of the desired product, 1-[3-(3-fluoropropyl) thiazoline-2-iminosulfonyl]-3-(4,6-dimethoxytriazin-2-yl) urea (1).

[EXAMPLE 3]

0.35 g (3.8 mmol) of phenol was dissolved in 40 ml of dry tetrahydrofuran, and 0.53 g (3.8 mmol) of chlorosulfonyl isocyanate was added under cooling with ice. The resulting solution was stirred at the same temperature for 20 minutes and then cooled to −40° C. Then, a mixture of 0.67 g (4.2 mmol) of 2-imino-3-(3-fluoropropyl)thiazoline (3), 0.43 g (4.2 mmol) of triethylamine and 15 ml of dry tetrahydrofuran was added dropwise. After the reaction solution was stirred at room temperature for 60 minutes, the solvent was distilled off under reduced pressure, and 50 ml of water was added. The liberated oily substance was extracted with 40 ml of chloroform three times, and the chloroform layer was washed with saturated aqueous salt solution and dried over anhydrous sodium sulfate. The solvent was distilled off under reduced pressure, and the residue was purified by preparative thin layer chromatography to obtain 200 mg of phenyl 3-(3-fluoropropyl)-thiazoline-2-iminosulfonylcarbamate (6: Y=Ph). Melting point 145°–147° C.

A mixture of 60 mg (0.22 mmol) of phenyl 3-(3-fluoropropyl)thiazoline-2-iminosulfonylcarbamate (6: Y=Ph), 34 mg (0.22 mmol) of 2-amino-4,6-dimethoxytriazine (2) and 8 ml of dry benzene was refluxed under heating for 3 hours, and then the reaction solution was cooled. The solvent was distilled off under reduced pressure, and the residue was washed with ether and acetonitrile to obtain 50 mg of the desired product, 1[(3-fluoropropyl) thiazoline-2-iminosulfonyl]-3-(4,6-dimethoxytriazin-2-yl) urea (1).

The dose of the compound of the present invention varies depending upon the application site, the season for application, the manner of application, the target weeds, the type of crop plants and the like. However, it is usually within a range of from 0.0001 to 1 kg, preferably from 0.001 to 0.5 kg per hectar (ha) as the amount of the active ingredient.

Further, the compound of the present invention may be combined with other herbicides, various insecticides, fungicides, plant growth regulators, synergists or safeners at the time of the preparation of the formulations or at the time of the application, as the case requires.

Particularly, combined use of the compound of the present invention with another agricultural chemical can be expected to result in lower cost attributable to reduction in the dose, a broader herbicidal spectrum and a higher herbicidal effect attributable to synergistic action of the combined chemical. In such a case, the compound of the present invention can be combined with plural known agricultural chemicals simultaneously. The agricultural chemicals which may be used in combination with the compound of the present invention, may be, for example, compounds disclosed in Farm Chemicals Handbook (1990).

When the compound of the present invention is used as a herbicide, it is usually mixed with a suitable carrier, for instance, a solid carrier such as clay, talc, bentonite, diatomaceous earth or white carbon, or a liquid carrier such as water, an alcohol (such as isopropanol, butanol, benzine alcohol or furfuryl alcohol), an aromatic hydrocarbon (such as toluene or xylene), an ether (such as an anisole), a ketone (such as cyclohexanone or isophorone), an ester (such as butyl acetate), an acid amide (such as N-methylpyrrolidone) or a halogenated hydrocarbon (such as chlorobenzene). If desired, a surfactant, an emulsifier, a dispersing agent, a penetrating agent, a spreader, a thickener, an antifreezing agent, an anticaking agent or a stabilizer may be added to prepare an optional formulation such as a liquid formulation, an emulsifiable concentrate, a wettable powder, a dry flowable, a flowable, a dust or a granule.

Now, examples of formulations of the compound of the present invention will be given. However, it should be understood that the present invention is by no means restricted to such specific examples. In the following Formulation Examples, "parts" means parts by weight.

| [Wettable powder] | |
|---|---|
| Compound of the present invention | 5–80 parts |
| Solid carrier | 10–85 parts |
| Surfactant | 1–10 parts |
| Others | 1–5 parts |

As the others, for example, an anticaking agent may be mentioned.

| [Emulsifiable concentrate] | |
|---|---|
| Compound of the present invention | 1–30 parts |
| Liquid carrier | 30–95 parts |
| Surfactant | 5–15 parts |

| [Flowable] | |
|---|---|
| Compound of the present invention | 5–70 parts |
| Liquid carrier | 15–65 parts |
| Surfactant | 5–12 parts |
| Others | 5–30 parts |

As the others, for example, an antifreezing agent and a thickener may be mentioned.

| [Granular wettable powder (dry flowable)] | |
|---|---|
| Compound of the present invention | 20–90 parts |
| Solid carrier | 10–60 parts |
| Surfactant | 1–20 parts |

| [Granule] | |
|---|---|
| Compound of the present invention | 0.1–10 parts |
| Solid carrier | 90–99.9 parts |
| Others | 1–5 parts |

| [Formulation Example 1] Wettable powder | |
|---|---|
| Compound of the present invention | 20 parts |
| Zeeklite A (trade name for a kaolin-type clay, manufactured by Zeeklite Industries, Co., Ltd.) | 76 parts |
| Sorpol 5039 (trade name for a mixture of nonionic and anionic surfactants, manufactured by Toho Chemical Industry Co., Ltd.) | 2 parts |
| Carplex (anticaking agent)(trade name for a white carbon, manufactured by Shionogi Pharmaceutical Co., Ltd.) | 2 parts |

The above ingredients were homogeneously pulverized and mixed to form a wettable powder.

| [Formulation Example 2] Wettable powder | |
|---|---|
| Compound of the present invention | 40 parts |
| Zeeklite A (trade name for a kaolin-type clay, manufactured by Zeeklite Industries, Co., Ltd.) | 54 parts |
| Sorpol 5039 (trade name for a mixture of nonionic and anionic surfactants, manufactured by Toho Chemical Industry Co., Ltd.) | 2 parts |
| Carplex (anticaking agent)(trade name for a white carbon, manufactured by Shionogi Pharmaceutical Co., Ltd.) | 4 parts |

The above ingredients were homogeneously pulverized and mixed to form a wettable powder.

| [Formulation Example 3] Emulsifiable concentrate | |
|---|---|
| Compound of the present invention | 5 parts |
| Xylene | 75 parts |
| Dimethylformamide | 15 parts |
| Sorpol 2680 (trade name for a mixture of nonionic and an anionic surfactants, manufactured by Toho Chemical Industry Co., Ltd.) | 5 parts |

The above ingredients were homogeneously mixed to form an emulsifiable concentrate.

| [Formulation Example 4] Flowable | |
|---|---|
| Compound of the present invention | 25 parts |
| Agrizole S-710 (trade name for a nonionic surfactant, manufactured by Kao Corporation) | 10 parts |
| Lunox 1000C (trade name for an anionic surfactant, manufactured by Toho Chemical Industry Co., Ltd.) | 0.5 part |
| 1% Rodopol water (trade name for a thickener, manufactured by Rhone-Poulenc) | 20 parts |
| Water | 44.5 parts |

The above ingredients were homogeneously mixed to obtain a flowable.

| [Formulation Example 5] Flowable | |
| --- | --- |
| Compound of the present invention | 40 parts |
| Agrizole S-710 (trade name for a nonionic surfactant, manufactured by Kao Corporation) | 10 parts |
| Lunox 1000C (trade name for an anionic surfactant, manufactured by Toho Chemical Industry Co., Ltd.) | 0.5 part |
| 1% Rodopol water (trade name for a thickener, manufactured by Rhône-Poulenc) | 20 parts |
| Water | 29.5 parts |

The above ingredients were homogeneously mixed to obtain a flowable.

| [Formulation Example 6] Granular wettable powder (dry flowable) | |
| --- | --- |
| Compound of the present invention | 75 parts |
| Isoban No. 1 (trade name for an anionic surfactant, manufactured by Kuraray Isoprene Chemical Co., Ltd.) | 10 parts |
| Vanilex N (trade name for an anionic surfactant, manufactured by Sanyo-Kokusaku Pulp Co., Ltd.) | 5 parts |
| Carplex #80 (trade name for a white carbon, manufactured by Shionogi Pharmaceutical Co., Ltd.) | 10 parts |

The above ingredients were homogeneously pulverized and mixed to form a dry flowable.

| [Formulation Example 7] Granule | |
| --- | --- |
| Compound of the present invention | 1 part |
| Bentonite | 55 parts |
| Talc | 44 parts |

The above ingredients were homogeneously mixed and pulverized, and after addition of a small amount of water, the mixture was kneaded, mixed and granulated by an extrusion-type granulating machine, followed by drying to obtain a granule.

The above wettable powders, emulsifiable concentrate, flowables and granular wettable powder are diluted with water from 50 to 1,000 times before application, and are applied at a dose of from 0.0001 to 1 kg a hectar (ha) as the amount of the active ingredient.

The compound of the present invention can be used as a herbicide for upland fields for sugar beet, in soil treatment, in soil incorporation treatment or in foliage treatment. Cropland weeds targeted by the compound of the present invention include broad-leaved weeds such as Solanaceous weeds (Solanaceae) represented by black nightshade (*Solanum nigrum*) and jimsonweed (*Datura stramonium*), Malvaceous weeds (Malvaceae) represented by velvetleaf (*Abutilon theophrasti*) and prickly sida (*Side spinosa*), Convolvulaceous weeds (Convolvulaceae) represented by morningglories (Ipomoea spps.) including common morningglory (*Ipomoea purpurea*) and bindweeds (Calystegia spps.), Amaranthaceous weeds (Amaranthaceae) represented by livid amaranth (*Amaranthus lividus*) and slender amaranth (*Amaranthus viridis*), Composite weeds (Compositae) represented by cocklebur (*Xanthium strumarium*), common ragweed (*Ambrosia artemisiaefolia*), sunflower (*Helianthus annuus*), hairy galinsoga (*Galinsoga ciliata*), creeping thistle (*Cirsium arvense*), common groundsel (*Senecio vulgaris*) and annual fleabane (*Erigeron annus*), Cruciferous weeds (Cruciferae) represented by India field cress (*Rorippa indica*), kedlock (*Sinapis arvensis*) and shepherd's purse (*Capsella Bursapastris*), Polygonaceous weeds (Polygonaceae) represented by tufted knotweed (*Polygonum Blumei*) and wild buckwheat (*Polygonum convolvulus*), Portulacaceous weeds (Portulacaceae) represented by common purslane (*Portulaca oleracea*), Chenopodiaceous weeds (Chenopodiaceae) represented by common lambsquater (*Chenopodium album*), figleaved goosefoot (*Chenopodium ficifolium*) and kochia (*Kochia scoparia*), Caryophyllaceous weeds (Caryophyllaceae) represented by common chickweed (*Stellaria media*), Scrophulariaceous weeds (Scrophulariaceae) represented by persian speedwell (*Veronica persica*), Commelinaceous weeds (Commelinaceae) represented by Asiatic dayflower (*Commelina communis*), Labiate weeds (Labiatae) represented by dead-nettle (*Lamium amplexicaule*) and red dead-nettle (*Lamium purpureum*), Euphorbiaceous weeds (Euphorbiaceae) represented by prostrate spurge (*Euphorbia supina*) and spotted spurge (*Euphorbia maculata*), Rubiaceous weeds (Rubiaceae) represented by false cleavers (*Galium spurium*), cleavers (*Galium aparine*) and indian madder (*Rubia akane*), Violaceous weeds (Violaceae) presented by violet (*Viola arvensis*), and Leguminous weeds (Leguminosae) represented by hempsesbania (*Sesbania exaltata*) and sicklepod (*Cassia obtusifolia*), Graminaceous weeds represented by shattercane (*Sorgham bicolor*), fall panicum (*Panicum dichotomiflorum*), johnsongrass (*Sorghum halepense*), barnyardgrass (*Echinochloa crusgalli*), large crabgrass (*Digitaria adscendens*), wild oat (*Avena fatua*), goosegrass (*Eleusine indica*), green foxtail (*Setaria viridis*) and water foxtail (*Alopecurus aegualis*), Cyperaceous weeds represented by purple nutsedge (*Cyperus rotundus*, *Cyperus esculentus*), and volunteer weeds represented by wheat (*Triticum vulgare*) and barley (*Hordeum vulgare*).

Now, the usefulness of the compounds of the present invention as a herbicide will be described in detail with reference to the following Test Examples.

[Test Example 1]

Test on the herbicidal effects in soil treatment

Plastic boxes having a length of 33 cm, a width of 33 cm and a depth of 8 cm were filled with sterilized diluvial soil, and seeds of wild oat, blackgrass, Italian ryegrass, wheat (volunteer weed), barley (volunteer weed), slender amaranth, common chickweed, cleavers, wild buckwheat, tufted knotweed, common lambsquater, kedlock and sugar beet were sown in each box and covered with soil in a thickness of about 1.5 cm. Then, herbicidal solution was applied onto the surfaces of the soil uniformly at predetermined doses in terms of the active ingredient. The herbicide solution was prepared by diluting a wettable powder appropriately formulated in accordance with the foregoing Formulation Examples with water and applied onto the entire soil surfaces by a small spray. Four weeks after the application, the herbicidal effects against each weed and the phytotoxicities on the crop plant were visually determined on the basis of the following standard ratings The results are shown in Table 1.

The compound of the present invention has selectivity for sugar beat.

Standard ratings:

5 . . . Mortality of more than 90% (almost completely killed)

4 . . . Mortality of from 70 to 90%

3 . . . Mortality of from 40 to 70%

2 . . . Mortality of from 20 to 40%

1 . . . Mortality of from 5 to 20%

0 . . . Mortality of less than 5% (almost ineffective)

The symbols have the following meanings.

A: wild oat, B: blackgrass, C: Italian ryegrass, D: wheat, E: barley, F: slender amaranth, G: common chickweed, H: cleavers, I: wild buckwheat, J: tufted knotweed, K: common lambsquater, L: kedlock a: sugar beet

[Test Example 2]

Test on the herbicidal effects in foliage treatment

Plastic boxes having a length of 33 cm, a width of 33 cm and a depth of 8 cm were filled with sterilized diluvial soil, and seeds of wild oat, blackgrass, Italian ryegrass, wheat (volunteer grass), barley (volunteer grass), slender amaranth, common chickweed, cleavers, wild buckwheat, tufted knotweed, common lambsquater, kedlock and sugar beet were sown in each box, and covered with soil in a thickness of about 1.5 cm. Then, the boxes were placed at room temperature of from 25° to 30° C. for 14 days to culture the plants, and a herbicide solution was applied to the foliages uniformly at predetermined doses in terms of the active ingredient. The herbicidal solution was prepared by diluting a wettable powder appropriately formulated in accordance with the foregoing Formulation Examples with water and applied onto the entire surfaces of the foliages by a small spray. Four weeks after the application, the herbicidal effects against each weed and the phytotoxicities on the crop plant were determined on the basis of the same standard ratings as in Example 1. The results are shown in Table 2.

The meanings of the symbols in Table 2 and the comparative compound are the same as in Example 1.

[Test Example 3]

Test on the herbicidal effects in foliage treatment in a field

Sugar beet was sown in rows in an upland field, and the interrow spaces were sown with wild oat, blackgrass, greenfoxtail, common lambsquater, common chickweed, slender amaranth, common lambsguater, kedlock, tufted knotweed, common purslane, wild buckwheat and cleavers, followed by soil incorporation of only the interrow spaces sown with the weeds. 25 Days after sowing of sugar beat and weeds, suspensions prepared by diluting wettable powders of herbicides with water were applied uniformly to the foliages so that each herbicide would be applied at predetermined doses. The applied water volume was 500 l/ha, and one unit area for treatment was 4 m². Before application, a nonionic surfactant was added to the suspensions to a concentration of 1000 ppm. 18 Days after the application, the herbicidal effects against each weed and the phytotoxicities on sugar beet were determined on the basis of the same standard ratings as in Example 1. The results are shown in Table 3.

The symbols in Table 3 have the following meanings.

A: wild oat, B blackgrass, M: green foxtail, K: common lambsquater, G: common chickweed, F: slender amaranth, L: kedlock, J: tufted knotweed, N: common purslane, I: wild buckwheat, H: cleavers, a: sugar beet

TABLE 1

| No. | Dose (kg/ha) | A | B | C | D | E | F | G | H | I | J | K | L | a |
|---|---|---|---|---|---|---|---|---|---|---|---|---|---|---|
| Compound of the | 0.01 | 0 | 0 | 0 | 0 | 0 | 4 | 0 | 0 | 0 | 0 | 0 | 0 | 0 |
| present invention | 0.04 | 2 | 3 | 2 | 2 | 0 | 5 | 5 | 5 | 0 | 0 | 5 | 3 | 0 |
| (1) | 0.16 | 5 | 5 | 5 | 3 | 3 | 5 | 5 | 5 | 3 | 5 | 5 | 5 | 0 |
| Comparative | 0.01 | 0 | 0 | 0 | 0 | 0 | 3 | 0 | 0 | 0 | 0 | 0 | 0 | 0 |
| compound | 0.04 | 0 | 0 | 0 | 0 | 0 | 5 | 0 | 0 | 0 | 0 | 0 | 5 | 0 |
| (A) | 0.16 | 1 | 3 | 5 | 5 | 0 | 5 | 5 | 0 | 3 | 0 | 5 | 5 | 0 |

Comparative Compound (A) which is disclosed in International Patent Publication WO93/00336

TABLE 2

| No. | Dose (kg/ha) | A | B | C | D | E | F | G | H | I | J | K | L | a |
|---|---|---|---|---|---|---|---|---|---|---|---|---|---|---|
| Compound of the | 0.0025 | 5 | 2 | 3 | 2 | 2 | 5 | 5 | 3 | 4 | 4 | 3 | 5 | 0 |
| present invention | 0.01 | 5 | 4 | 5 | 3 | 5 | 5 | 5 | 5 | 5 | 5 | 5 | 5 | 0 |
| (1) | 0.04 | 5 | 5 | 5 | 5 | 5 | 5 | 5 | 5 | 5 | 5 | 5 | 5 | 0 |
| Comparative | 0.0025 | 0 | 0 | 0 | 0 | 0 | 2 | 0 | 0 | 0 | 0 | 0 | 2 | 0 |
| compound | 0.01 | 3 | 2 | 2 | 2 | 0 | 5 | 5 | 2 | 3 | 2 | 2 | 5 | 0 |
| (A) | 0.04 | 4 | 3 | 5 | 3 | 2 | 5 | 5 | 4 | 4 | 4 | 5 | 5 | 0 |

Comparative Compound (A) is the same as in Test Example 1.

TABLE 3

| No. | Dose (kg/ha) | A | B | M | K | G | F | L | J | N | I | H | a |
|---|---|---|---|---|---|---|---|---|---|---|---|---|---|
| Compound of the present invention (1) | 0.025 | 5 | 5 | 4 | 5 | 5 | 5 | 5 | 5 | 5 | 5 | 5 | 0 |
| | 0.05 | 5 | 5 | 5 | 5 | 5 | 5 | 5 | 5 | 5 | 5 | 5 | 0 |
| | 0.10 | 5 | 5 | 5 | 5 | 5 | 5 | 5 | 5 | 5 | 5 | 5 | 0 |
| Comparative compound (A) | 0.05 | 5 | 4 | 4 | 5 | 5 | 5 | 5 | 5 | 4 | 5 | 5 | 0 |
| | 0.10 | 5 | 5 | 5 | 5 | 5 | 5 | 5 | 5 | 5 | 5 | 5 | 0 |
| | 0.20 | 5 | 5 | 5 | 5 | 5 | 5 | 5 | 5 | 5 | 5 | 5 | 0 |
| Comparative compound (B) | 0.025 | 0 | 5 | 4 | 3 | 5 | 2 | 5 | 5 | 2 | 5 | 5 | 0 |
| | 0.05 | 0 | 5 | 4 | 3 | 5 | 3 | 5 | 5 | 4 | 5 | 5 | 0 |
| | 0.10 | 1 | 5 | 5 | 4 | 5 | 5 | 5 | 5 | 4 | 5 | 5 | 0 |
| | 0.20 | 1 | 5 | 5 | 4 | 5 | 5 | 5 | 5 | 4 | 15 | 5 | 0 |

Comparative Compound (A) is the same as in Test Example 1

Comparative Compound (B) is a technical grade of the active ingredient (represented by following formula) of a herbicide for sugar beet commercially available under the trade name. SAFARI. and was synthesized by Nissan Chemical Industries, Ltd.

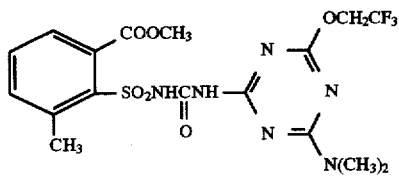

We claim:

1. A fluoropropylthiazoline represented by the following formula or a salt thereof.

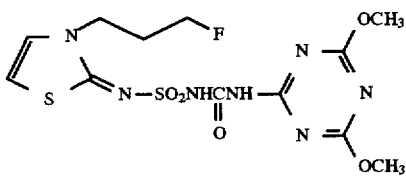

2. A selective herbicide composition comprising a herbicidally effective amount of the compound of claim 1 and an agriculturally acceptable carrier.

3. A method of controlling growth of a harmful plant in a sugar beet field, comprising applying to said field a herbicidally effective amount of the compound of claim 1.

4. A method of controlling growth of a harmful plant in a sugar beet field, comprising applying to said field a herbicidally effective amount of the composition of claim 2.

* * * * *